United States Patent [19]

Schwartz

[11] Patent Number: 5,405,519
[45] Date of Patent: Apr. 11, 1995

[54] PULSED ORIENTED ELECTROPHORESIS

[75] Inventor: David C. Schwartz, Baltimore, Md.

[73] Assignee: New York University, New York, N.Y.

[21] Appl. No.: 879,551

[22] Filed: May 4, 1992

Related U.S. Application Data

[63] Continuation of Ser. No. 244,897, Sep. 15, 1988, abandoned.

[51] Int. Cl.$^6$ .................. G01N 27/26; G01N 27/447
[52] U.S. Cl. ........................... 204/299 R; 204/182.8
[58] Field of Search ........................ 204/299 R, 182.8

[56] References Cited

U.S. PATENT DOCUMENTS

| | | | |
|---|---|---|---|
| 4,473,452 | 9/1984 | Cantor et al. | 204/299 R X |
| 4,737,251 | 4/1988 | Carle et al. | 204/182.8 |
| 5,084,157 | 1/1992 | Clark et al. | 204/299 R |

FOREIGN PATENT DOCUMENTS

| | | |
|---|---|---|
| 2605472 | 4/1988 | European Pat. Off. |
| 8701955 | 5/1984 | |
| 8700635 | 1/1987 | WIPO |
| 8402001 | 9/1987 | WIPO |

OTHER PUBLICATIONS

McPeek, Jr., F. D. "Separation of Large DNA Molecules by Modified Pulsed Field Gradient Gel Electrophoresis" Analytical Biochemistry 156 (1986) 274–285.

Schwartz, et al., "Conformational Dynamics of Individual DNA Molecules During Gel Electrophoesis", Nature, Apr. 6, 1989, pp. 520–522.

Primary Examiner—John Niebling
Assistant Examiner—John S. Starsiak, Jr.
Attorney, Agent, or Firm—Cushman Darby & Cushman

[57] ABSTRACT

Disclosed herein is a method of electrophoretically separating particles by the application to pulsed field electrophoresis of a pulsing routine in which the pulses are modulated in such a way as to define the effective field angle of the particles undergoing separation as determined by the vector sum of the pulses. In one embodiment of the invention, pulse times are modulated to define the orientation of the particles undergoing separation. In a second embodiment, the intensities of the pulses are modulated to define the orientation of the particles. The method of the invention allows the simple and dynamic determination of effective field angle by pulsing routine rather than by placement of an electrode array. In addition, the invention makes it possible for the first time to translate particles undergoing separation incrementally through a gel matrix.

2 Claims, 15 Drawing Sheets

Fig. 6a
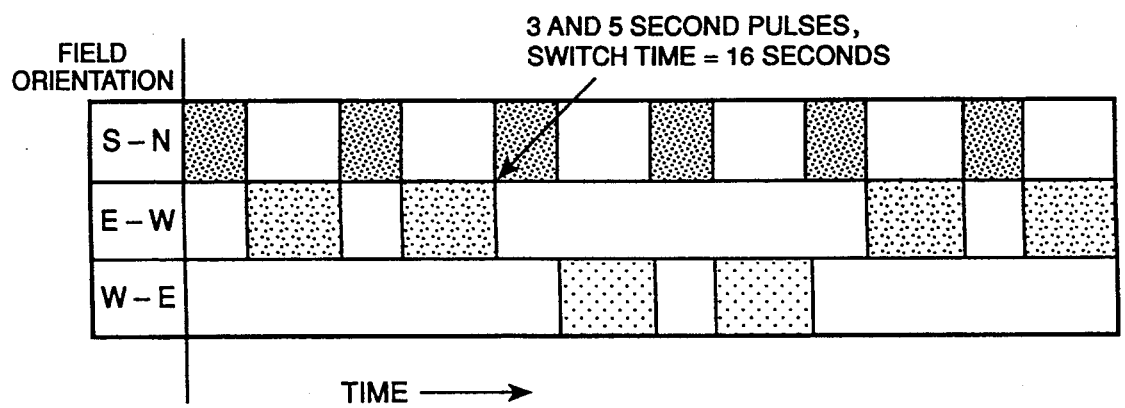
Fig. 6b
Fig. 6c
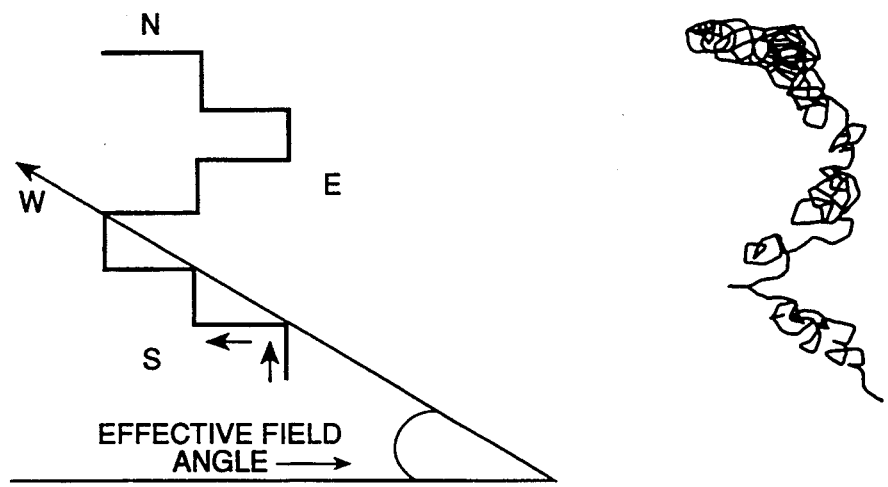

3  2  1

4  3  2  1

PULSED ORIENTED ELECTROPHORESIS

This is a continuation of application Ser. No. 07/244,897, filed on Sep. 15, 1988, which was abandoned upon the filing hereof.

BACKGROUND OF THE INVENTION

This invention was made with government support under Contract No. GM37277 awarded by the National Institute of General Medical Sciences of the United States Department of Health and Human Services. The government has certain rights in this invention.

The invention is in the field of electrophoresis. It is of particular interest in terms of its applications in genetic engineering and molecular biology.

The invention, which is a new kind of pulsed field electrophoresis, makes it possible to determine the effective field angle of the particles undergoing separation by pulsing routine, rather than by placement of an electrode array. In addition, the present electrophoretic technique makes it possible for the first time to translate particles undergoing separation incrementally through a gel matrix. Additionally, the invention makes it possible to separate with a high degree of resolution and at high speeds larger particles (molecules) than those capable of resolution using conventional pulsed field electrophoresis, and to separate particles in a selectable narrow range of sizes (molecular weight).

Electrophoresis in which particles such as a mixture of macromolecules are moved, for example, through a gel matrix, by an electric field, is a widely-used technique for qualitative analysis and for separation, recovery and purification. It is particularly important in the study of chromosomes, proteins and nucleic acids.

It is known that the DNA molecules which make up chromosomes exist in solution as random coils, which resemble loose bunches of yarn moving about in the thermal environment of the solution. Such a DNA coil 10 is shown in FIG. 1. The hydrodynamic radius of a large DNA molecule, as measured by sedimentation or light scattering, can be enormous. For example, a 600 kb (kb=kilobase pair, a unit of length for nucleic acids consisting of 1,000 nucleotide pairs) DNA molecule is approximately $4 \times 10^{-4}$ cm in diameter, while an agarose gel pore has an approximate diameter of $1 \times 10^{-5}$ cm.

During electrophoresis, the large random coils of the DNA molecules must be deformed by an electric field in order to pass through a gel matrix 12 in the form of a compressed aligned coil 14. Using the technique of the disclosed invention as described below, it has now been shown for the first time that during electrophoresis, a DNA coil 10 compresses into a series of blobs 16 as shown in FIG. 2. The blobs 16 each contain as much as 10 kb of DNA. A train of blobs 16 migrates in an aligned fashion through the gel matrix 12. The degree of alignment of the blob train is determined by the electric field strength and varies as $E^2$.

Previous to now, there has not been disclosed an effective method for the electrophoretic separation of very large particles. For example, using previously known electrophoretic techniques, the size of the largest DNA molecule routinely handled is 2,000 kb, although a maximum size of 10,000 kb is possible.

Using conventional gel electrophoresis, DNA molecules up to approximately 50 kb, or the size of lambda bacteriophage DNA, may be separated. Because of its relatively large pore size ($1 \times 10^{-5}$ cm, as noted above) and because it does not bind DNA molecules, agarose is the matrix of choice. Separation is usually performed in a horizontal or vertical gel and the migration of molecules is size dependent up to approximately 50 kb. Above this size, DNA molecules tend to run with a common mobility; that is, all large DNA molecules run together in a gel.

Although particles of higher mass (i.e., up to approximately 600 kb) can be resolved by reducing the gel concentration to as low as 0.035% and reducing field strength, there are drawbacks to this method. Most notably, the dramatic reduction in gel concentration adversely affects resolution, and makes experimental conditions difficult to control. In addition, an electrophoretic run using a reduced gel concentration and field strength can take a week or more to complete.

Pulsed field electrophoresis, developed by the present inventor and described in U.S. Pat. No. 4,473,452 (the disclosure of which is hereby incorporated by reference and relied upon), improves the separation of large DNA molecules in a gel matrix. According to this technique, deliberately alternated electric fields, rather than the uniform fields sought in previously known electrophoretic methods, are used to separate particles. More particularly, particles are separated using electric fields of equal strength which are transverse to each other, which alternate between high and low intensities out of phase with each other at a frequency related to the mass of the particles and which move the particles in an overall direction transverse to the respective directions of the fields. (It should be noted here that the term "transverse" as used herein is not limited to an angle of, or close to, 90°, but includes other substantial angles of intersection.)

Thus, an electric field is pulsed between alternate sets of electrodes, forcing the periodic relaxation and reorientation of the particles undergoing separation. Pulse times are approximately equal to the molecular reorientation times for achieving molecular size resolution. When the direction of the electric field is changed, small particles quickly orient themselves and start a new migration along the new path. Larger particles, on the other hand, remain substantially immobile until they are reoriented in the direction of the electric field. Then, they too begin to move in the new direction. By that time, the smaller particles will have moved ahead of them. Thus, separation by size occurs.

Using the technique of the present invention, it is now possible for the first time to directly determine the dynamic molecular conformation of individual particles, for example, DNA molecules, in a gel matrix as oriented by a specially modulated electric field. Using fluorescence microscopy/image processing as described below in Example 5, it has been determined that during pulsed field electrophoresis, the blob train of a DNA molecule orients with the applied electric field in a very complicated manner and during this process, electrophoretic mobility is retarded until alignment is complete. Upon field direction change, the blob train moves in several new directions simultaneously (i.e., the blobs appear to be moving somewhat independently). Eventually, some part of the blob train dominates in reorienting with the applied field and pulls the rest of the blobs along its created path through the gel matrix. The time necessary for complete blob train alignment varies directly with size; i.e., a 10 mb (1 mb=1,000 kb) molecule requires one hour to reorient, while a 10 kb molecule requires only ten seconds, using similar field strengths.

The length of the pulse in each direction determines the size of the molecules that will separate from each other. A fast pulse will cause small molecules to separate, while a slow pulse will cause large molecules to separate. Thus, changing the pulse time selectively modulates the electrophoretic mobility of the molecules in a size dependent manner.

For a given molecular weight, electrophoretic mobility is modulated by varying the pulse time. The minimum measured mobility is obtained when the pulse time is equal to the orientation time. This is called the resonance time. Because the blob train orientation process retards mobility during orientation, the maximum amount of retardation occurs when the pulse time equals the orientation time. However, if the pulse time exceeds the orientation time, then only a portion of the mobility suffers the orientation retardation effects, resulting in increased mobility. Finally, when the pulse time is less than the orientation time, the blob train does not have sufficient time to fully orient, which results in an intermediate orientation as determined by the two applied fields. Thus, the amount of orientation that a blob train requires to fully orient with a given applied field is minimized, and since orientational effects retard velocity, the resulting mobility is increased relative to the resonance time induced mobility, but less than conventional gel electrophoresis.

The angle between applied fields in pulsed field electrophoresis is known to have a profound effect upon separation, although the molecular basis for separation dependence on field angle (the angle measured between two alternately applied fields) remains obscure. Molecules below about 600 kb resolve fairly well when the field angle is 90°. However, obtuse angles give the best separations for molecules larger than about 650 kb.

Schwartz and Cantor (Cell, 37:67-75, 1984) designed pulsed electrophoresis apparatus utilizing field gradients. A field gradient is a variation of field strength over a measured distance, i.e., volts/cm$^2$. As a consequence of using field gradients, the angle between the two applied fields varied from 90° to 135°. The average angle a molecule experiences in this apparatus is obtuse. Although resolution was adequate, the field gradients caused extensive distortion of the DNA banding patterns, wherein the DNA did not migrate in straight lanes, but in curvilinear paths, which made it difficult to compare adjacent bands.

Researchers later eliminated band distortion by using two homogeneous (ordinary) electrical fields oriented at 120° to each other. As with the above mentioned field gradient approach, both instruments are capable of resolving up to approximately 10,000 kb.

Lane distortions can also be eliminated using Field Inversion Gel Electrophoresis (FIGE) or Reverse Field Electrophoresis (RFE), wherein the field is periodically reversed through a 180° angle. This method differs from other variations of pulsed field electrophoresis in that the alternate pulse times are not equal; i.e., the forward pulse times are longer than the backward pulse times. The range of molecular weights that can be resolved using this method is limited to approximately 1,200 kb.

Thus, despite the fact that pulsed field electrophoresis has provided improved results in the electrophoretic separation of particles, it has been known for some time that the method suffers from important limitations, e.g., human chromosomally sized DNA molecules (100 mgb; 1 mgb=1,000 kb) cannot be resolved using pulsed field electrophoresis. Although the need to overcome the limitations of the prior art has also been known for some time, no previous proposals have been put forward which successfully overcome such limitations.

SUMMARY OF THE INVENTION

This invention is directed to a method of electrophoretically separating deformable particles by the application to pulsed field electrophoresis of a pulsing routine in which the pulses are modulated to define the effective field angle incurred by the particles undergoing separation as determined by the vector sum of the pulses. In one embodiment of the invention, pulse times are modulated to define the orientation of a particle undergoing separation. In a second embodiment, the intensities of the pulses are modulated to define the orientation of the particle.

The invention is based on the surprising discovery that highly desirable results are yielded by the application to conventional pulsed field electrophoresis of such a pulsing routine, wherein a series of alternating pulses is used to translate, for example, the blob train of a DNA molecule incrementally through a gel matrix (i.e., the blob train can be moved a single blob diameter or less at each pulse).

One of the important advantages of this new technique, called pulsed oriented electrophoresis (POE), is that it allows the simple and dynamic determination of the effective field angle of the particles undergoing separation by pulsing routine, rather than by placement of an electrode array. This permits experiments, such as, the abovementioned imaging of DNA molecules during gel electrophoresis using fluorescence microscopy, that would otherwise be impossible to perform. Another important advantage of the new technique is that particles undergoing separation can be moved incrementally through the gel matrix. In contrast, using conventional pulsed field electrophoresis, only the overall movement of the particles as a whole can be modulated to yield any molecular separation. Another significant advantage of the new technique is that it dramatically extends the mass range of particles that can be electrophoretically separated at high resolution. As a non-limiting example, the new technique can resolve particles as large as 12,000 kb (see Example 2), while the upper limit of conventional pulsed field electrophoresis is about 10,000 kb. An additional advantage is that the new electrophoretic technique can resolve, in the same gel, particles in a narrower mass range as compared to conventional pulsed field electrophoresis. As a non-limiting example, the new technique can resolve simultaneously, in the same gel, DNA molecules in the size range of 350 to approximately 850 kb, while having virtually no resolution in the 200 to 350 kb range and simultaneously in the 850 to 2500 kb range (see Example 4; 30,30-60 second separations). The separation profile can thus be described as being sigmoidal, as compared to conventional electrophoresis (see FIG. 3).

These and other advantages of the invention, as well as additional inventive features, will become apparent from the detailed description which follows the Brief Description of the Drawings.

The invention is illustrated in detail in the following drawings which are included for illustrative purposes and should not be considered to limit the invention.

BRIEF DESCRIPTION OF THE DRAWINGS

FIG. 6 illustrates a pulsing routine which can be used according to the present invention; FIG. 6(a) illustrates the step and switch times and the field orientation of the exemplified pulsing routine (3 and 5 second pulses with a 16 second switch time; shaded boxes show field on in given orientation); FIG. 6(b) shows the effective field angle produced by the vector sum of the pulses of FIG. 6(a); and FIG. 6(c) shows the typical conformation of a particle undergoing separation according to the pulsing routine of FIG. 6(a).

FIG. 17 shows the DNA molecular conformational changes during gel electrophoresis of G bacteriophage as revealed by the fluorescence microscopy experiments described in Example 5.

FIG. 18 is a schematic illustration of the instrumentation used in the study of the electric birefringence of DNA molecules during gel electrophoresis.

DETAILED DESCRIPTION OF THE INVENTION

As noted above, the electrophoretic method of the present invention, called pulsed oriented electrophoresis (POE), is a new kind of pulsed field electrophoresis. The present invention is based on the surprising discovery that highly desirable results are yielded by the application to conventional pulsed field electrophoretic techniques as set forth, for example, in U.S. Pat. No. 4,473,452, of a pulsing routine wherein the alternating pulses are modulated to translate a deformable particle incrementally through a gel matrix. Thus, unlike conventional pulsed field electrophoresis, which relies on simple alternating pulses of corresponding time periods and equal intensities to effect separation, the present method relies on pulsing routines in which the alternating pulses are modulated in such a way as to define, both simply and dynamically, the effective field angle of the particles undergoing separation as determined by the vector sum of the pulses. In one embodiment of the invention, pulse times are modulated to define the orientation of the particles undergoing separation. In a second embodiment, the intensities of the pulses are modulated to define the orientation of the particles.

Figure 1:
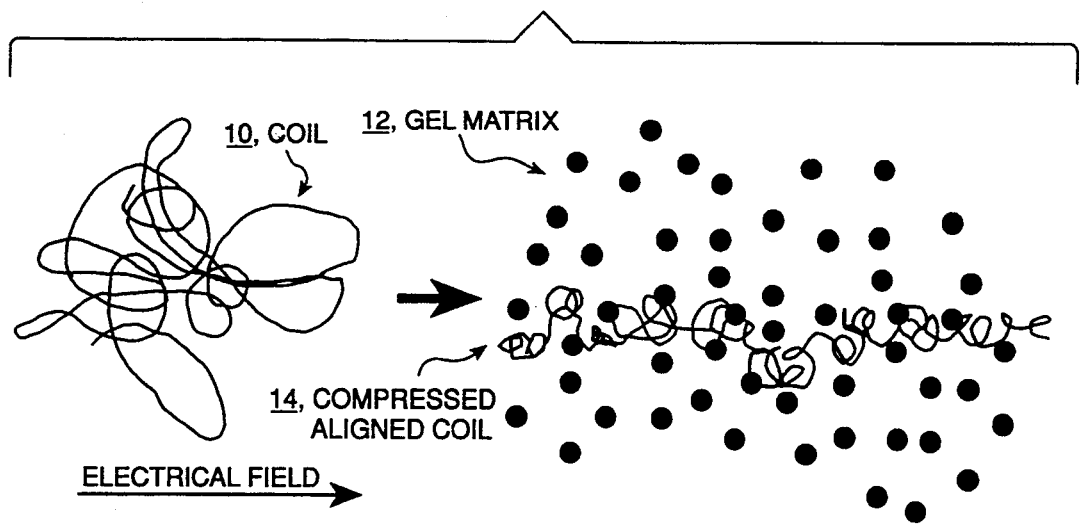
FIG. 1 is a schematic drawing illustrating DNA compression and alignment in a gel matrix.
Figure 2:
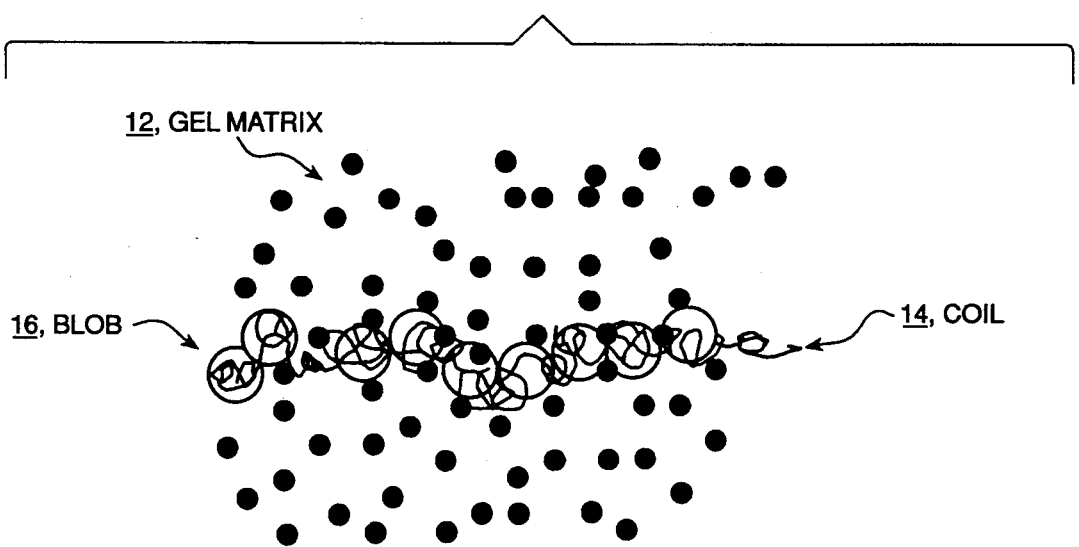
FIG. 2 is a schematic drawing illustrating a series of blobs making up a DNA coil.
Figure 3A:
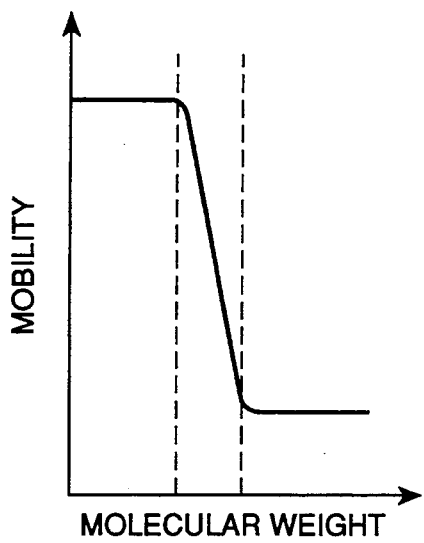
FIG. 3 shows a comparison of Orthogonal POE separation (FIG. 3(a)) and conventional pulsed field electrophoretic separation (FIG. 3(b)). The dashed line in FIG. 3(a) indicates the narrow range of resolution obtained using this method.
FIG. 3(b) shows the broad separation obtained using conventional pulsed field electrophoresis.
Figure 3B:
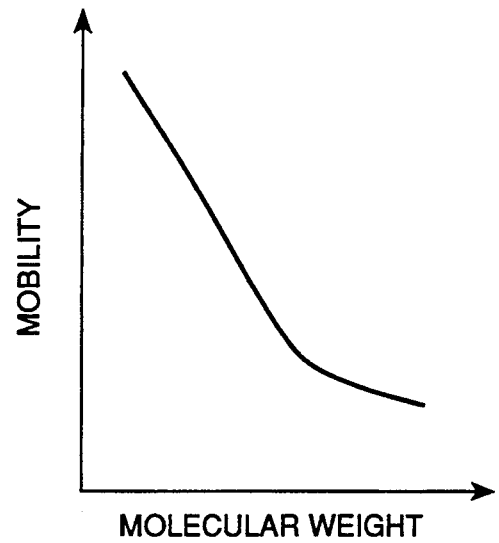
Figure 4:
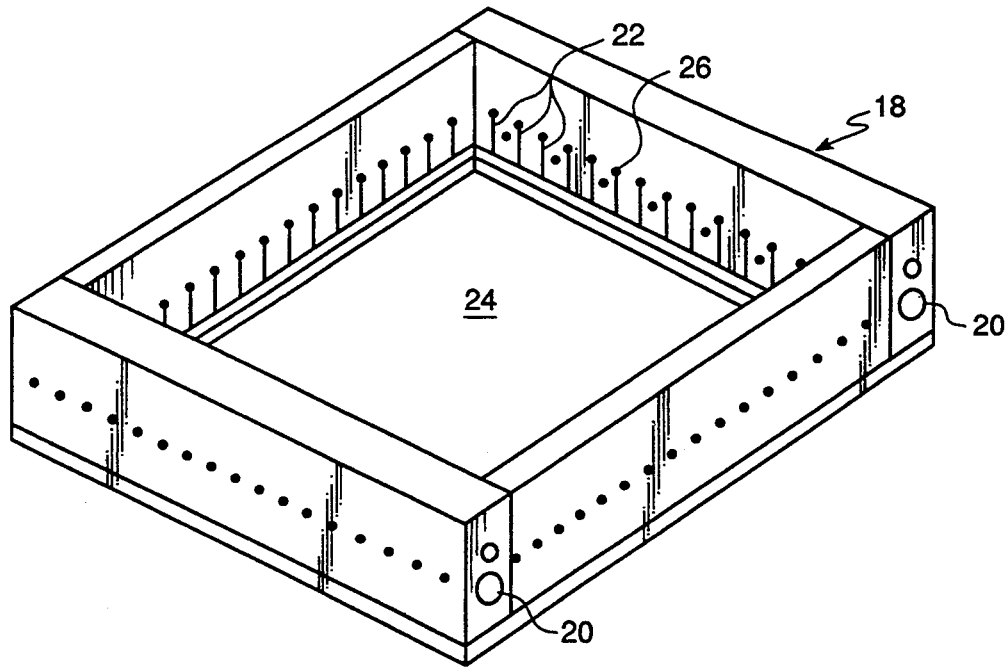
FIG. 4 is a perspective view of an electrophoresis chamber useful in explaining certain features of the invention.
Figure 5:
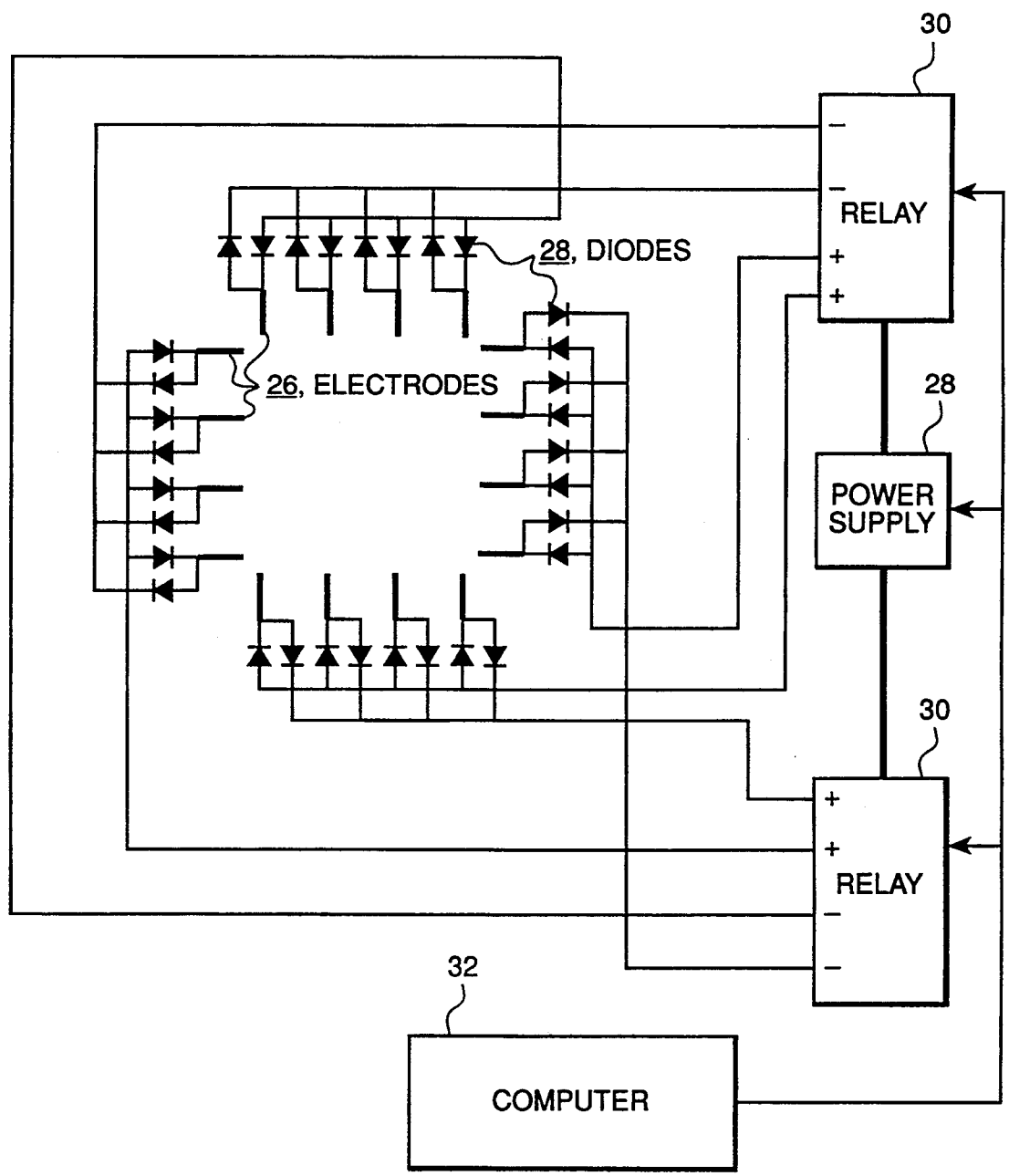
FIG. 5 is a partly schematic and partly block diagram showing an interconnection of exemplary chamber electrodes.

Any instrument suitable for use in pulsed field electrophoresis can be used according to the present invention. An exemplary laboratory instrument is illustrated in FIG. 4 in a perspective view. The instrument comprises an opentop, rectangular electrophoresis chamber 18 made of an electrically insulating material, such as ½ inch plexiglass, with dimensions of approximately 8 inches by 8 inches. The instrument has buffer circulation input and output 20 and buffer circulation ports 22. It has a space 24 for the slab gel (preferably agarose gel or acrylamide gel) commonly used in electrophoresis, surrounded by electrodes 26 which are connected to diodes as depicted in FIG. 5. The electrodes are thin (0.032 inch) platinum wires which extend vertically about ¾ inch each and are arranged about 2.5 cm apart.

As one example, the electrode wires can enter the chamber through respective holes arranged in a horizontal row about ⅜ inch above the interior bottom of the chamber, with each wire extending down, along a respective interior side wall, to the interior bottom of the chamber. In order to generate the desired electrical fields, electrodes 26 are interconnected as shown in FIG. 5. In particular, d-c power supply 28 (such as Electronic Measurements Model TCR600S1.6, Neptune, N.J.) supplies d-c power to relays 30 (such as DPDT, 115 volt a-c relays) which are controlled by a computer 32 (such as Adtron DGS-16 pulse generator installed in an IBM AT computer, or Lindberg Enterprises Chrontrol 4-Channel CT Series) to connect selected outputs to the d-c power from power supply 28. Computer 32 also controls d-c power supply 28 so that the potential of the power supply can be varied. Outputs of relays 30 are connected to electrodes 26 (as seen in FIG. 5), through respective diodes 34 for each electrode.

The instrument exemplified in FIG. 5 differs from that described in U.S. Pat. No. 4,473,452 essentially in its use of two sets of diodes 34 which enables bipolar operation of the discrete electrode array. The diodes 34 can be replaced by a large multiganged relay (not shown) to provide similar electrical isolation. However, it is best to use the diodes 34 when very fast (less than 1 second) pulsing is needed. As in the case of the instrument described in U.S. Pat. No. 4,473,452, the presently exemplified instrument generates electrical fields which are orthogonal to each other, which alternate between high and low intensities out of phase with each other according to the chosen pulsing routine as described below and which translate the particles undergoing separation incrementally through the gel matrix in an overall direction transverse to the respective directions of the generated electrical fields. Due to the novel bipolar nature of the electrode design, it is now possible for the first time to change polarities, simultaneously if desired, in addition to alternating high and low intensities without any significant electrode induced field distortions.

The pulsing routines of the present invention, their determination of the effective field angle of the particles undergoing separation, as well as their effect on the incremental translation of the particles through the gel matrix, are best described by reference to FIG. 6 which illustrates, as a non-limiting example, one particular pulsing routine wherein the pulse times are modulated to define the orientation of a particle undergoing separation.

The pulsing routine illustrated by FIG. 6(a) is as follows: a 3 second S-N pulse is followed by a 5 second E-W pulse, which is followed by a 3 second S-N pulse, which is followed by a 5 second E-W pulse. These short orienting pulses are 90°. For example, S. cerevisiae chromosomes are separated with excellent results using a pulsing routine of 60 second N-S, 60 second E-W-E step times and 120 second switch time (step ratio=1). This method has the additional advantage of a faster running time. For example, using a field angle of 90°, yeast chromosomes can be resolved in one quarter (1 day vs. 4 days) the running time using 60° field angles as generated by POE. In addition, the OPOE method can be used to separate particles closer in size than is possible using the POE method. Thus, the OPOE effect can be exploited to provide a precise and dramatic separation in a narrow size range, as shown in Example 4. The advantages of a relatively narrow range of separation can be useful when critically separating molecules very close in size.

To obtain excellent separation over a very broad size range, the use of a program consisting of different switching times coupled with appropriate step times (=switch time/2) is effective. For example, a combination of 60,60-120 second, 30,30-60 second and 15,15-30 second pulses provides superb separation for the entire S. cerevisiae genome (200–2500 kb in size, 16 chromosomes).

To emulate the separation obtained with pulsed field electrophoresis using obtuse (120°) field angles, an orienting pulse ratio of 3:5 can be used with longer overall directional switching time. For example, pulsing 3 seconds N followed by a 5 second pulse W, repeated for a total of 120 seconds (or 15 sets of pulses) and then pulsing 3 seconds N followed by 5 seconds E for a total of 120 seconds will produce a net trajectory similar to conventional pulsed field electrophoresis. called the step time (expressed as a ratio and/or absolute time, and similar in operation to the field angle of conventional pulsed field electrophoresis). The step time is therefore a measure of the time durations of the individual pulses used to orient the object. The series of pulses i collectively referred to herein as the switch time (functionally similar to the pulse time of conventional pulsed field electrophoresis), which in this case is 16 seconds. A following switch time includes another 3 second S-N pulse alternates with a 5 second W-E pulse for a switch time of 16 seconds, following which a 3 second S-N pulse alternates again with a 5 second W-E pulse for a switch time of 16 seconds.

For the purpose of illustration, pulsing is then discontinued and the effective field angle as determined by the pulsing routine exemplified in FIG. 6(a) is shown in FIG. 6(b). Effective field angle herein means the angle of orientation of the electric field caused by the pulses. It is defined as double the trajectory of the particles. In this Figure, the direction of the arrows correspond to the field orientation as determined by the pulsing routine of FIG. 6(a) and the length of the arrows is proportional to the respective switch times. The coil orientation, or incremental translation, of the particle undergoing separation (in this case, switch time is less than resonance time) is shown in FIG. 6(c).

As further examples, it is noted that if pulses are equal in duration, then the resulting trajectory of the particle undergoing separation is 45° (90° effective field angle); if the pulses have a ratio of 3:5, then the trajectory is 60° (120° effective field angle). If the step time equals half the switch time (this variation of the POE method is called Orthogonal POE or OPOE), an effective field angle of 90° (step ratio=1) is produced. The step ratio is therefore defined as a ratio between the step times of the two differently oriented pulses.

Dramatic separations of large DNA molecules can be produced using effective field angles of Varying the step time can affect size resolution. If the step time (=1 step ratio, summed, e.g., 3 seconds N, 5 seconds E-W-E=8 second step time) is less than the switching time, then the POE method becomes somewhat equivalent to conventional pulsed field electrophoresis in that variables such as pulse time and field strength are comparable to give similar separations. Varying the step time but maintaining the same step ratio does not have a dramatic effect upon resolution. This observation holds for yeast chromosomal DNA molecules which range in size from 200 to 2,500 kb on 16 chromosomes, with pulsing routines including a switching time of 120 seconds and step times ranging from milliseconds to 8 seconds.

With larger DNA molecules, the step time has a more pronounced effect on separation. For example, chromosomal DNA molecules obtained from *S. pombe* (containing 3 large chromosomes; 3, 5 and 8 mgb in size) show different separations when run out under identical conditions (3,600 second switch time, 2 volts/cM field strength) with only the step times changed: 30,50 seconds vs. 3,5 seconds. The longer step time results in increased electrophoretic mobility and greater resolution of the 8 mgb chromosomal DNA molecule. The superior high molecular weight resolution does not stem from running a greater distance in the gel; rather, the longer step time provides better resolution in this size range.

Low field strength appears to be necessary for successful resolution of DNA molecules larger then 3 mgb. For example, *S. pombe* have not been resolved at a field strength significantly greater than about 3 volts/cM. Generally speaking, the optimum pulse time or switching time needed to minimize mobility (or resonance time) is inversely proportional to the field strength. For example, typical conditions for separating yeast chromosomes using the POE method are: 120 volts (about 6 volts/cM field strength using an electrophoresis chamber such as that exemplified in FIGS. 4 and 5) and a 120 second switch time (3,5 second step time); however, a 240 second switch time fusing 60 volts would give similar separation results.

The determination of effective field angle by pulsing routine rather than by placement of an electrode array permits experiments that would otherwise be impossible to perform. As noted above, and as described in Example 5 below, the present inventor has been able to image DNA molecules during gel electrophoresis using fluorescence microscopy. The apparatus used is essentially a small POE electrophoresis chamber mounted on a microscope stage. At the present time, the effect of field angle on DNA electrophoretic conformation is being studied and varying the field angle by moving electrodes as taught by conventional pulsed field electrophoresis is not practical due to microscope stage physical constraints. However, using the present technique, the field angle can be varied by simply adjusting the pulse programming to provide the desired angle.

Similarly, the present technique has been applied with success to electrophoretic birefringence studies, as described in Example 6. The present inventor is currently developing a new spectroscopic method to size DNA molecules that may replace gel analytical electrophoresis. A polarized light is being used to directly determine the dynamic molecular conformation of DNA molecules in a gel matrix as oriented by an applied electrical field. The instrumentation uses in part, a small electrophoresis chamber. As in the case of the imaging of DNA molecules using fluorescence microscopy, there is a need for control of field angle and the POE method using the miniature POE instrument (identical to that exemplified in FIGS. 4 and 5, with the exception that the miniature POE instrument measures 1 square inch) is uniquely well suited for this application due to the ability of the bipolar isolated electrodes, as described herein, to allow back and forth motions of the DNA particles, without any electrode-induced field distortion in the POE chamber. The back and forth motion of the DNA particles is a key feature of the POE chamber, and keeps the sample from moving out of the laser radiation as well as allowing for very. convenient control of field angle.

In a second embodiment of the invention, the intensities of the pulses are modulated to define the orientation of the particles undergoing separation. This variation of POE, called Multiple Potential Pulsed Electrophoresis (MPPE), operates in an analogous fashion to POE, with the exception that it is pulse intensities which are modulated rather than the pulse times. As a non-limiting example, using MPPE, a 3,3 second step time can be used with a field ratio of 3:5 (i.e., 30 volts N-S, 50 volts E-W-E). This is functionally equivalent to a 3,5 second step time (functionally as judged by separation). Absolute and relative field strengths are controlled during a run in an analogous fashion to dynamic pulse control.

The dynamic control of the field angle obtained using the present technique makes it possible to effect unique separations by varying the field angle during a run. There are many ways to vary the field angle, including:

1) changing the field angle during one switch time interval;
2) changing the field angle through many switch time intervals;
3) changing the field angle in one step interval (this results in placing steps within steps); and
4) changing both field intensity and switch time (a combination of POE and MPPE).

At this time, the first two options have been found to have a marked effect, allowing for the first time the dynamic control of field angle. The second two options are expected to show similar marked effects also allowing dynamic control of the field angle.

The present invention will be illustrated in detail in the following examples. These examples are included for illustrative purposes and should not be considered to limit the present invention.

EXAMPLE 1

Figure 7:
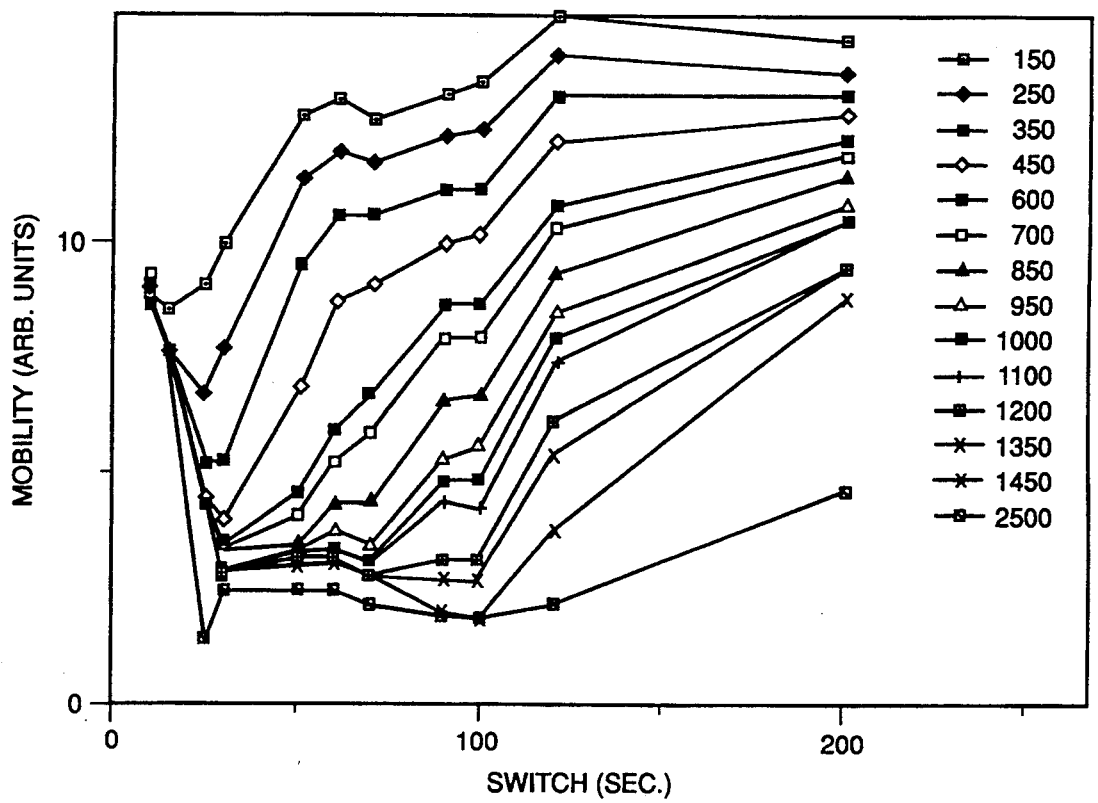
FIG. 7 is a graph illustrating the variation of electrophoretic mobility of yeast chromosomes with changes in switch time. Chromosome sizes range from 150 kb to 2500 kb.

Resolution and Selective Change of Electrophoretic Velocities of Large DNA Molecules Change of electrophoretic mobility of yeast chromosomal molecules with change of switch time is illustrated in FIG. 7. The plots shown in this Figure were generated by running 9 gels, each containing identical yeast chromosomal DNA molecules consisting of 16 differently sized molecules of (which 14 were resolved, ranging in size from 150 kb to 2500 kb) with the same general electrophoretic conditions as follows: 120 volts (4.25 volts/cM, field strength), 1.0% high gelling temperature agarose (FMC Corp.), $\frac{1}{2} \times$ TBE buffer, a step time of 3 seconds N-S with 5 seconds E-W-E, and identical instrumentation, as depicted in FIGS. 4 and 5. The only variable modified between the different runs was the switch time. Velocities were obtained by measuring the band locations on photographs of ethidium bromide stained gels.

Figure 8:
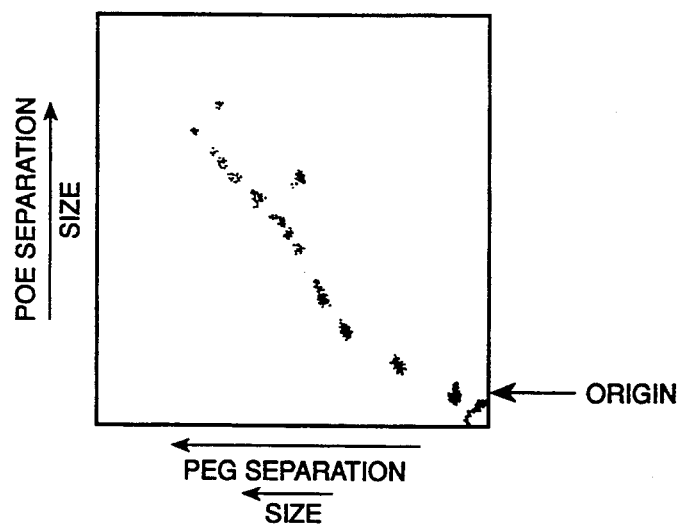
FIG. 8 illustrates pulsed field electrophoresis size resolution of S. cerevisiae chromosomal DNA molecules followed by POE separation at a 3,5 second step time and a 120 second switch time.

To observe any mobility inversions that sometimes occur (i.e., when a smaller molecule electrophoresis more slowly than a large molecule), *S. cerevisiae* chromosomal DNA molecules were first prepared using the insert method and then size resolved using conventional pulsed field electrophoresis. A strip of gel containing the resolved molecules (consisting of approximately 14 bands) was cut from the pulsed field electrophoresis gel and cast into the POE gel for further analysis. The resolved molecules were then run at a 3,5 second step time and a 120 second switch time. Separation of the molecules according to size is shown in FIG. 8, where pulsed field electrophoresis separation is shown along the horizontal axis and POE separation is shown along the vertical axis.

Relative size separations can be seen along the vertical axis of the graph of FIG. 7. A review of Figure shows that the switch time can be varied to modulate electrophoretic separation and that the POE method can resolve large DNA molecules as well as selectively change electrophoretic velocities.

Figure 9:
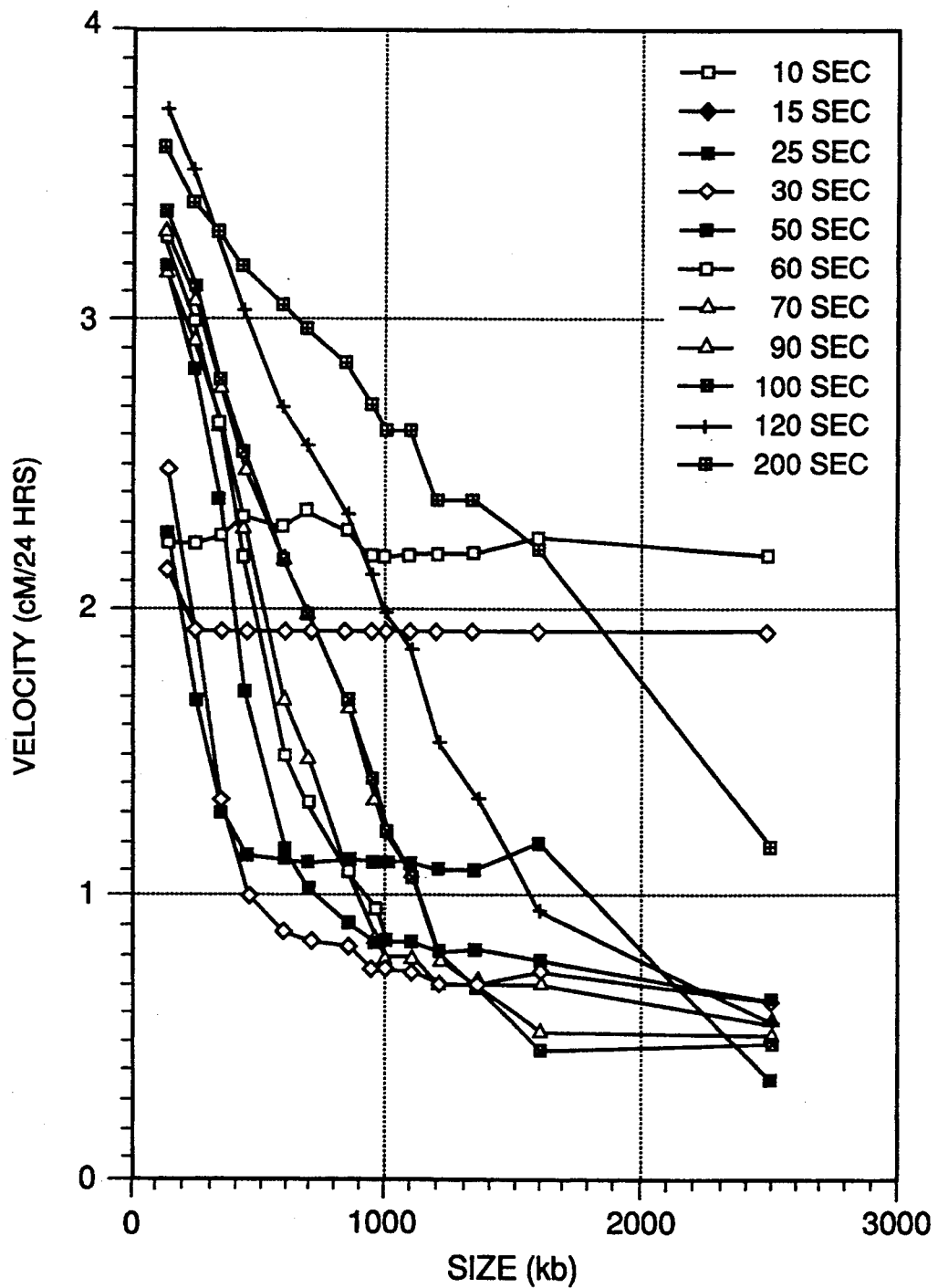
FIG. 9 is a graph showing the data of FIG. 7 plotted with different axes: velocity vs. size for a variety of switch times.

FIG. 9 shows the data of FIG. 7 plotted with different axes: velocity vs. size for a variety of switch times, ranging from 10 seconds to 200 seconds. Thus, this graph shows the change of velocity with molecular size for a given pulse time.

EXAMPLE 2

Figure 10:
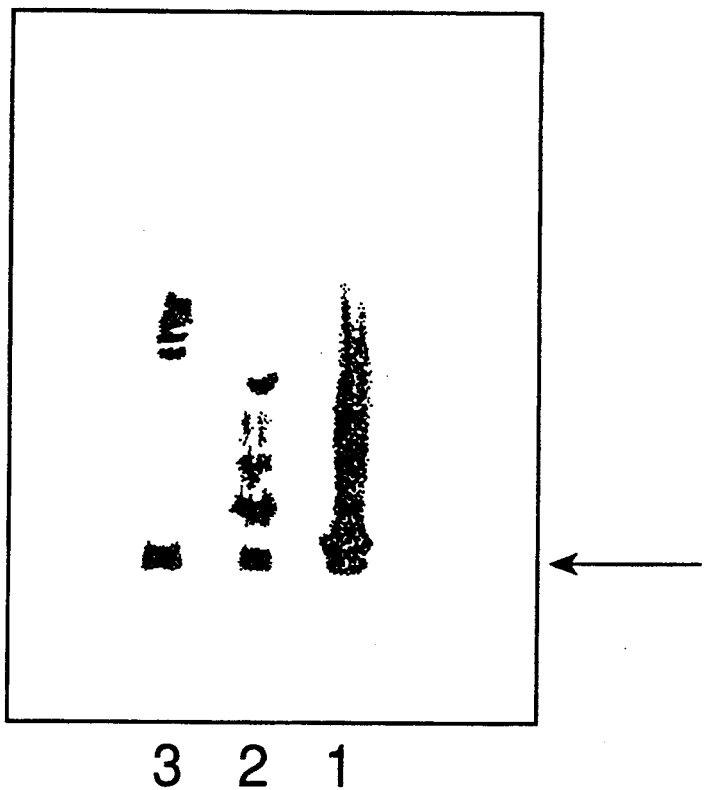
FIG. 10 shows POE separation of 12,000 kb human DNA molecules.

Separation of Ultra-Large DNA Molecules, Including Human DNA, Using the POE Method Samples of S. pombe and S. cerevisiae, prepared according to the methods described in Example 2, were loaded in lanes 2 and 3, respectively (shown in FIG. 10). Lane 1 contained a Not I restriction enzyme digest of human white blood cells prepared by embedding washed human white blood cells in agarose inserts (with a concentration of approximately 5 micrograms of human DNA per gel insert) and then soaking the inserts with 50 units of the restriction enzyme in a standard restriction enzyme buffer overnight. The reaction was terminated by decanting the restriction enzyme-buffer mixture and adding excess 0.5M EDTA (pH=9.5) and 1% sarkosyl detergent. The reaction cleaved the DNA at specific sites to produce a series of very large fragments. Electrophoresis conditions were as follows: 1.0% low gelling temperature gel in $\frac{1}{2}\times$TBE, a step time of 30 seconds N-S with 50 seconds E-W-E, a 3,600 second switch time, a 1 volt/cm field strength and a 10 day running time, using the instrumentation depicted in FIGS. 4 and 5.

The arrow in FIG. 10 shows the presence of a distinct band at least 12,000 kb in size, relative to the largest pombe chromosome (lane 2). The digest was judged to be complete by Southern blot analysis with appropriate hybridization of human DNA sequences (data not shown). This is the largest DNA molecule to be size fractionated by any method.

EXAMPLE 3

Resolution of Very Large DNA Molecules

Figure 11:
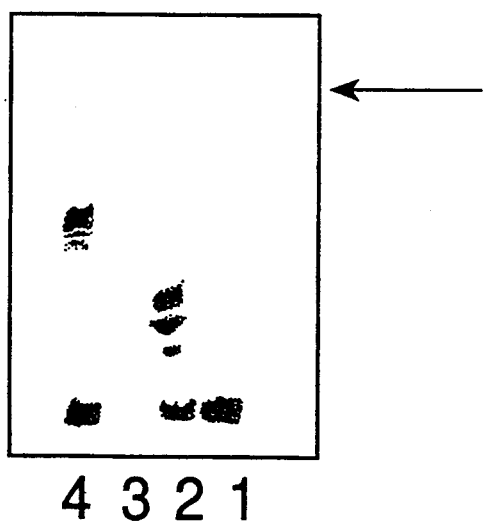
FIG. 11 shows the ethidium stained gel of Example 3. Lanes 1 and 2 show the separation of S. pombe chromosomal DNA molecules from strains SP518 and SP553, respectively. Lane 4 shows the separation of S. cerevisiae (strain Ph3-6D) chromosomal DNA molecules.

S. pombe DNA was prepared according to the method used in preparing the S. cerevisiae of Example 1, with the exception that an additional step was included in order to remove the tough cell wall with NovoZym 234 (Novo Laboratories, Denmark), an enzyme preparation. S. pombe inserts were loaded into a 1% low gelling temperature agarose gel (FMC, Corp.), and electrophoresis conditions were as follows: a step time of 30 seconds N-S with 50 seconds E-W-E, a 3,600 second switch time, 1 volt/cM field strength and the instrumentation depicted in FIGS. 4 and 5. The resulting ethidium stained gel is shown in FIG. 11. The separation of chromosomal DNA molecules as shown in FIG. 11 demonstrates the ability of the POE method to size resolve very large DNA molecules.

EXAMPLE 4

Separation of Large DNA Molecules Using the OPOE Method

The following experiments were performed to characterize the effect of a step ratio of 1 (pulse length N-S:pulse length E-W-E) by varying the step time (total time N-S plus E-W-E) relative to the switch time. All experimental conditions were identical to those described in Example 1, with the exception that the step ratios were equal to 1.

Figure 12:
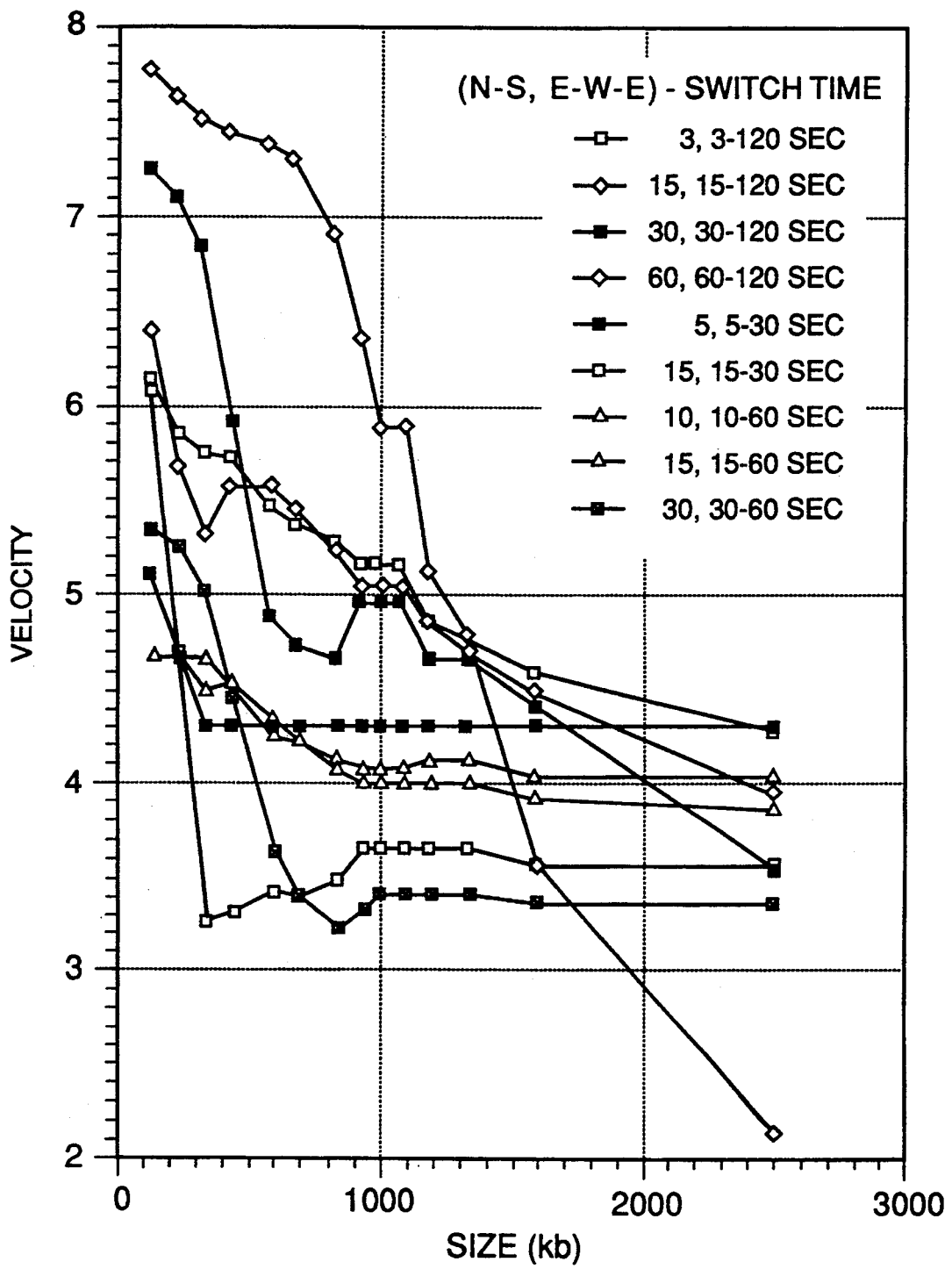
FIG. 12 is a graph illustrating the experiments performed using the Orthogonal POE method as described in Example 4. This is a composite graph illustrating the different switch times and step times as shown in FIGS. 13-15. All step ratios are equal to 1.

The results of the experiments are shown in FIGS. 12-15. FIG. 12 is a composite graph of different switch times with differing step times. This Figure shows a rather complicated relationship between all of the different variables. It is particularly noted that the 60,60-120 second line shows tremendous resolving power in the 900-2500 kb range and poor resolution elsewhere.

Figure 13:
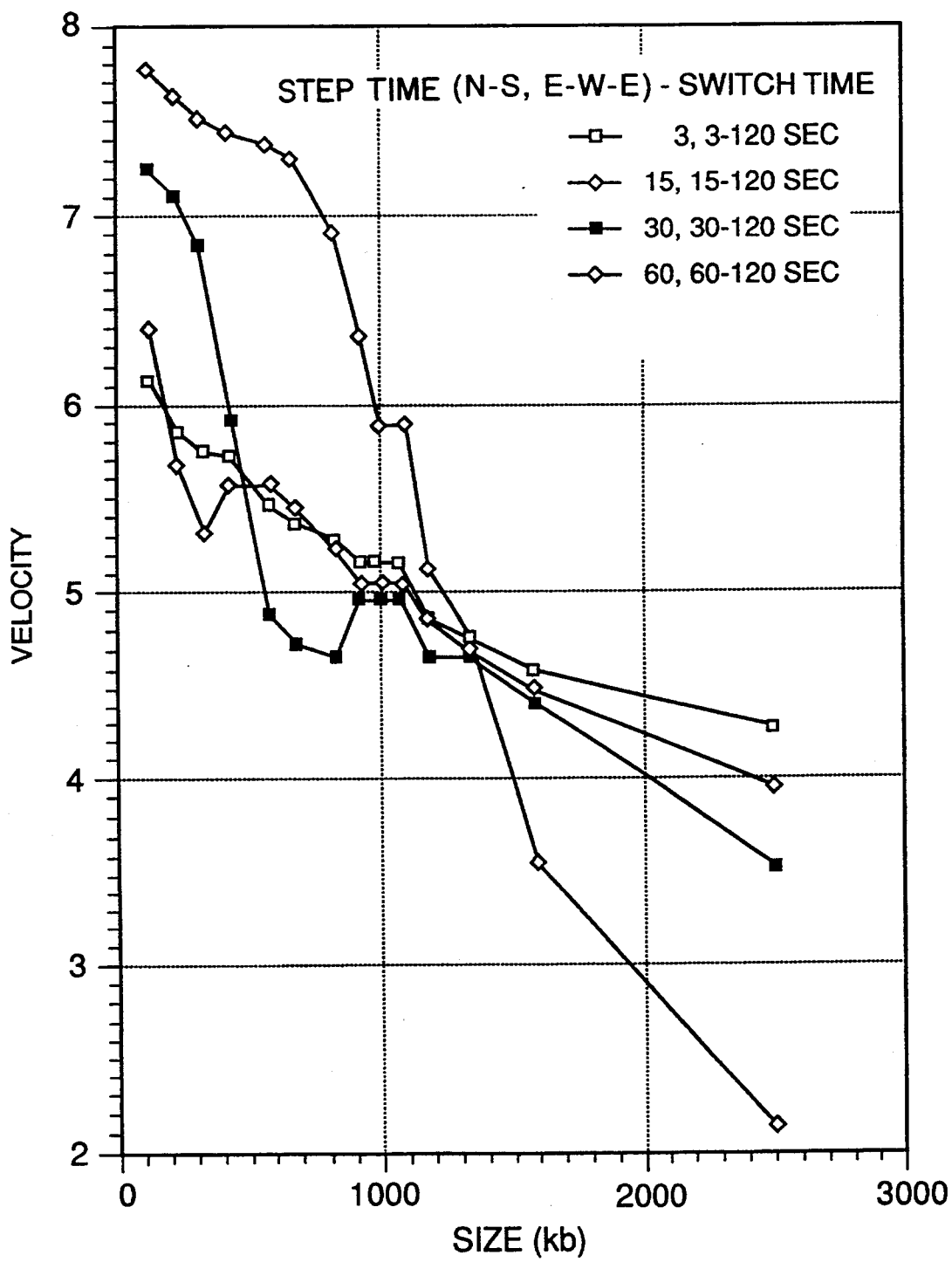
FIG. 13 is a graph illustrating 3,3-120 second, 15,15-120 second, 30,30-120 second, and 60,60-120 second pulses.
Figure 14:
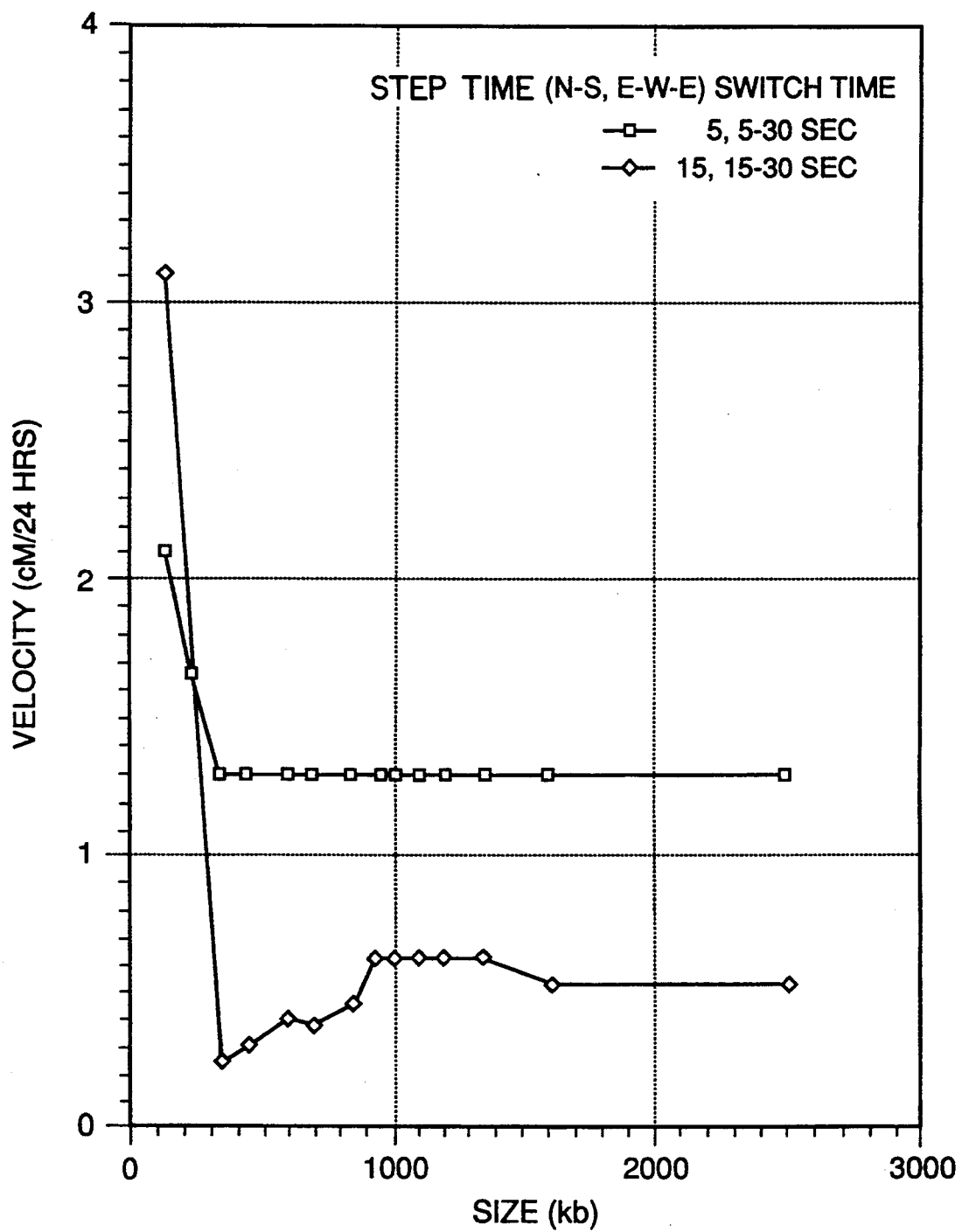
FIG. 14 is a graph illustrating 5,5-30 second and 15,15-30 second pulses.
Figure 15:
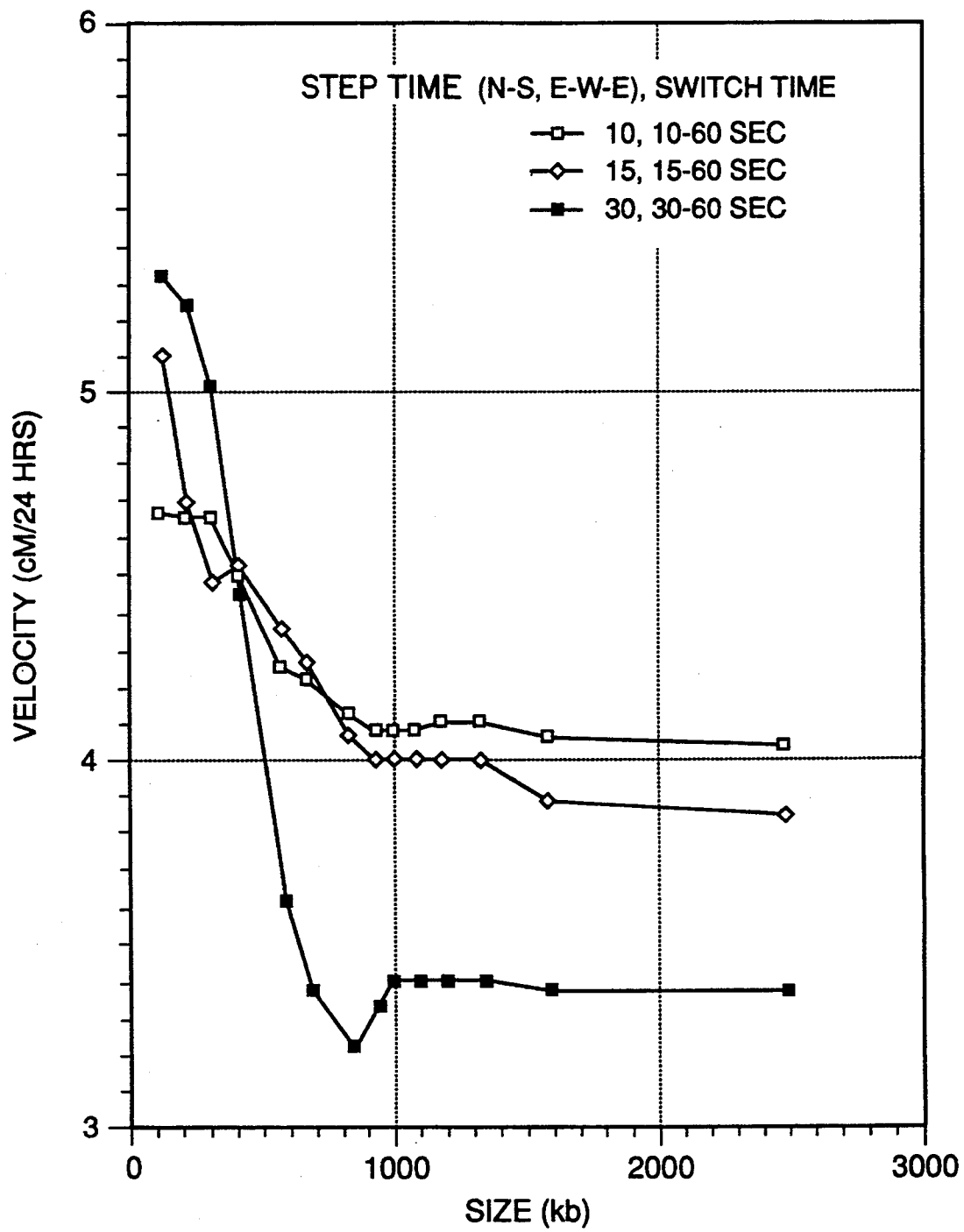
FIG. 15 is a graph illustrating 10,10-60 second, 15,15-60 second and 30,30-60 second pulses.

FIGS. 13-15 group the data by step time. FIG. 13 shows the best resolution in the 700-2500 kb range. FIG. 14 shows excellent resolution in the 200-400 kb range (15,15 second step time, and 30 second switch time), while FIG. 15 shows maximum resolution in the 400-800 kb range (30,30 second step time, and 60 second switch time).

As may be seen from a review of FIGS. 12-15, the range of resolution using the POE method, as defined by the selected combinations of switch time and step ratio, is relatively narrow in comparison to that of, for example, the POE results presented in FIG. 9.

EXAMPLE 5

The POE Method Used to Study DNA Molecular Conformational Changes During Gel Electrophoresis as Revealed by Fluorescence Microscopy It is possible to view single DNA molecules stained with an appropriate chromophore, such as 4',6-diamidino-2-phenylindole dihydrochloride (DAPI), using epifluorescence microcopy. In other words, light microscopy can visualize single molecules using fluorescence to a resolution of approximately 0.2 microns. In this experiment, epifluorescence microscopy was coupled with the POE method to study DNA conformational changes during electrophoresis. The POE method using the adapted microscopy chamber shown in FIG. 16 was essential to these studies because it could generate a wide variety of effective field angles. Beyond the usual constraints of varying field angles, the microscope stage presented additional limitations due to inherent space constraints. The POE method using the adapted chamber could also dynamically and rapidly change these angles, if required.

Figure 16:
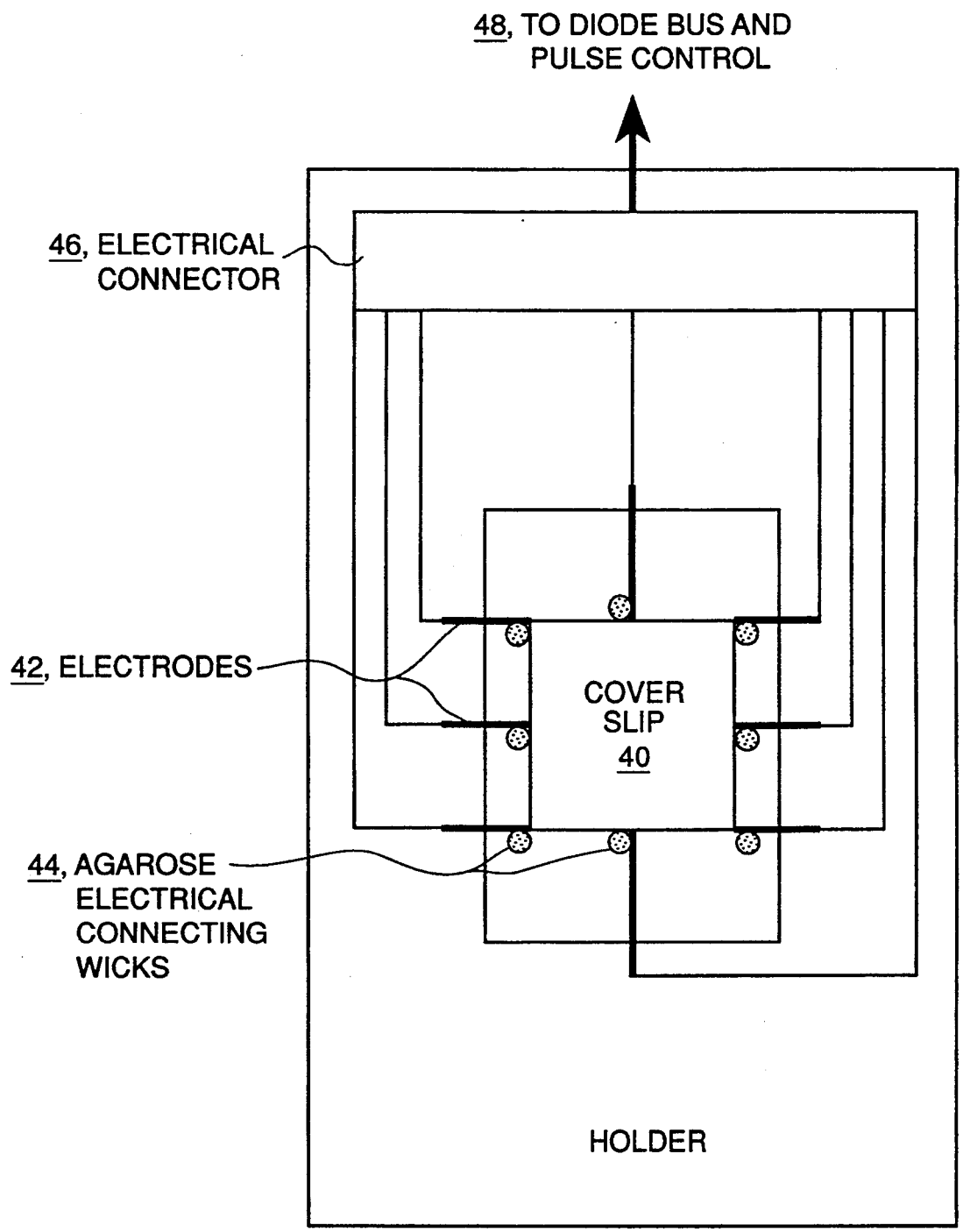
FIG. 16 is a schematic drawing of a POE microscopy chamber which can be used in fluorescence microscopy studies.

FIG. 16 shows a diagram of the adapted POE chamber with a slide holding a small quantity of an agarose gel—DNA mixture (3–10 microliter) enclosed by a standard cover slip (glass, 18×18 mm) 40. The holder, complete with sample, fits neatly on a standard microscope stage. A slide is placed into the holder (made of glass or plexiglass) and the platinum electrodes 42 make electrical contact with the gel slide-cover slip sandwich placing drops of 30% glycerol-agarose at the agarose electrical connecting wicks 44. The glycerol prevents drying out of the gel. The holder electrical connector 46 provides a link to the bipolar diodes and pulsing instrumentation 48 (not shown) which are identical to that previously presented in FIG. 5.

FIG. 17 shows reproductions of three photographs of G bacteriophage DNA (630 kb) embedded in 1.0% low gelling temperature agarose (⅓×TBE buffer) according to different POE conditions (using the POE chamber shown in FIG. 16) and stained with DAPI. The images were obtained with a Zeiss (Germany) Axioplan microscope using epifluorescence utilizing a Zeiss Model 487902-000 filter pack, and a zeiss 100×Plan Neofluar oil immersion objective. The resulting images were intensified by a Hamamatsu C-2400 silicon intensified target video camera (Hamamatsu Photonics, Japan), thereby enabling low light level operation. The signal from the video camera was fed to an image processor (Inovision Corp., Triangle Park, N.C.) for digitization, storage and further data processing, including image enhancement. The photographs of FIG. 17 were shot from a video monitor.

To facilitate the interpretation of the photographs, schematic drawings have been placed to the right of their respective sources.

Figure 17A:
FIG. 17(a) shows 3 distinct DNA molecules after 3 minutes of conventional electrophoresis.
Figure 17A:
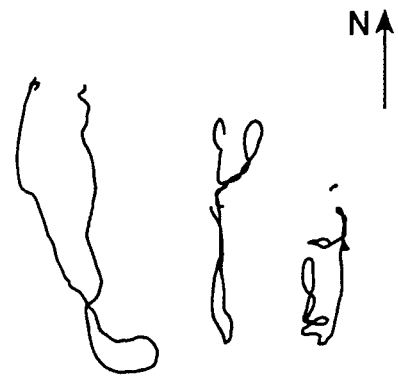

FIG. 17(a) shows three distinct DNA molecules after 3 minutes of conventional electrophoresis with an applied field strength of about 3 volts/cm, in the S-N direction (indicated by the arrow on the right-hand side of the drawing). The molecules are greatly stretched out in the field direction and are folded over.

Figure 17B:
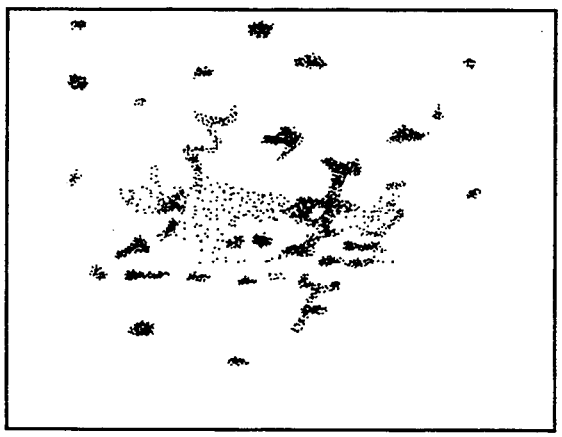
FIG. 17(b) demonstrates the DNA conformational changes after 3 minutes of POE (3 seconds W, 5 seconds N-S-N and a switch time of 40 seconds).
Figure 17B:
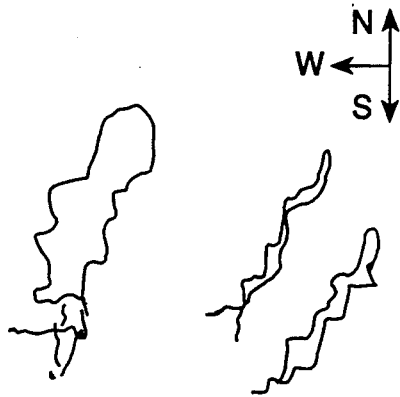

FIG. 17(b) demonstrates the DNA conformational changes during a typical POE experiment (after 3 minutes of electrophoresis): 3 seconds W, 5 seconds N-S-N, a switch time of 40 seconds and a field strength of 3 volts/cm. The photograph shows three distinct DNA molecules, with an average orientation of approximately 60° as expected from the given POE conditions. A comparison of these molecules with FIG. 17(a) shows the presence of steps with a size ratio (vertical to horizontal distance) indicative of field duration caused by the changing field direction. Delivering pulses with a smaller step ratio will produce smaller DNA steps (the steps are clearly visible in the photograph). Generally, the POE treated molecules are more condensed than their conventional electrophoresis treated counterparts. These results show unequivocally, that the POE method does actually orient molecules the gel to any desired orientation.

Figure 17C:
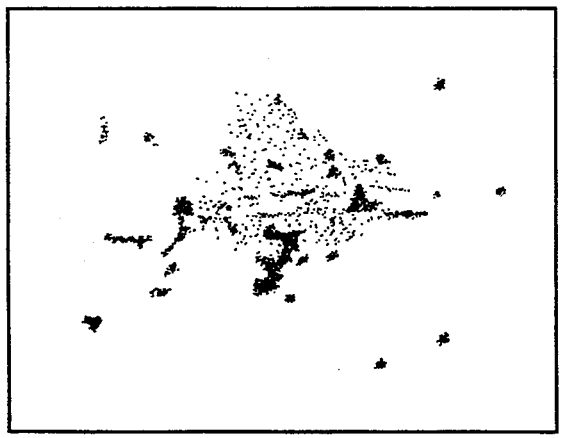
FIG. 17(c) shows the effect of pulsing 40 seconds N followed by 40 seconds W. Schematic drawings, facilitating the interpretation of the photographs, are to the right of their respective sources.
Figure 17C:
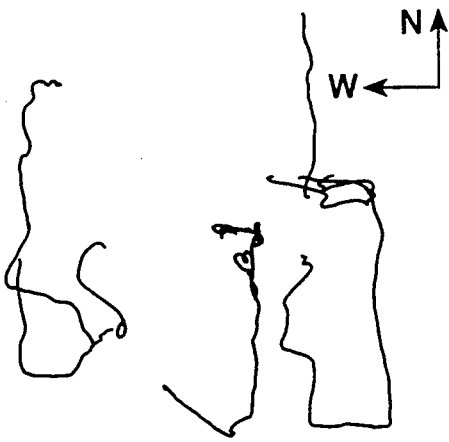

FIG. 17(c) shows the effect of pulsing N 40 seconds followed by a 40 second W pulse (the same conditions described above, in relation to FIG. 17(b)). Again, there are three distinct molecules presented. The molecules are well oriented by the pulses into a series of orthogonal sections. Additionally, the molecules appear as more stretched out than in the previous experiment.

EXAMPLE 6

The POE Method Used to Study the Electric Birefringence of DNA Molecules During Gel Electrophoresis The orientation of DNA molecules in a gel during electrophoresis can be studied by observing the change of refractive index (birefringence). When an electrical field is applied, the DNA molecules stretch out and align with the field, thereby changing the refractive index. By measuring the change of birefringence with time, it is possible to understand details of DNA blob train motion as the molecule orients with the applied electrical field.

Figure 18A:
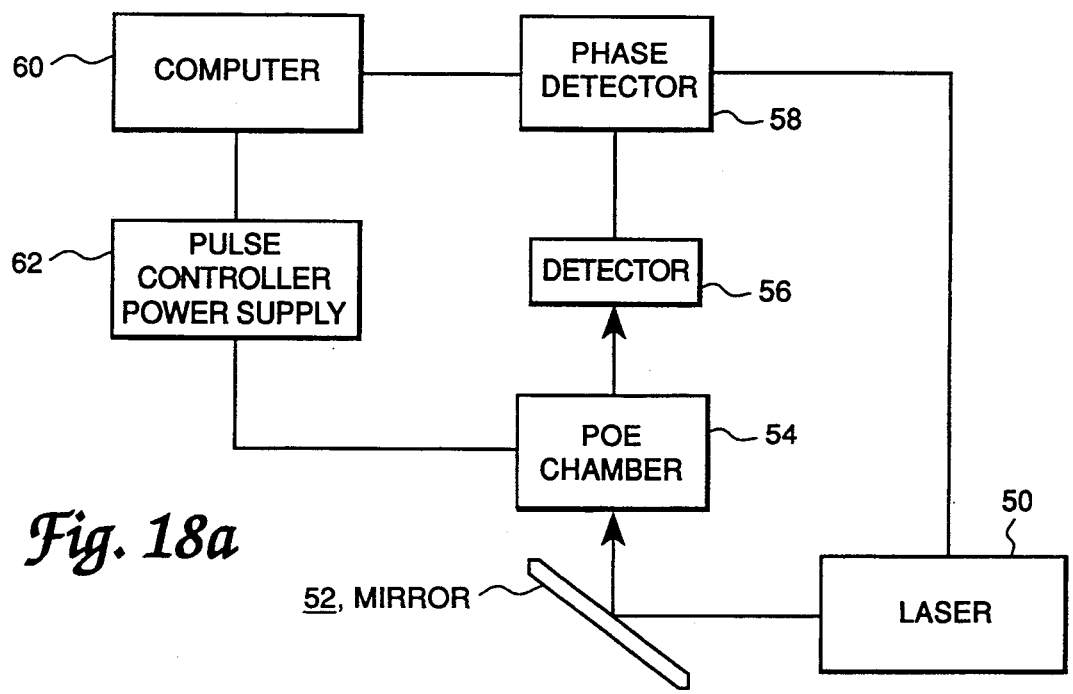
FIG. 18(a) is a diagram of the instrumentation as described in Example 6.
Figure 18B:
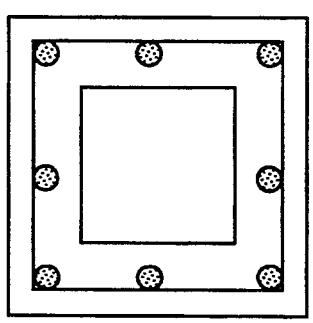
FIG. 18(b) is a top view of the POE chamber. The interior shaded square is the gel insert containing DNA, and the circles show the electrode positions.
Figure 18C:
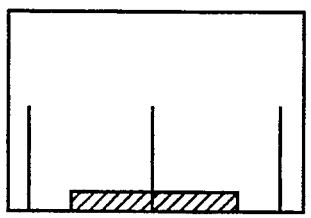
FIG. 18(c) is a side view looking through the POE chamber, with the lines showing the electrode position.

The birefringence measurements of the present experiment were made by determining the phase difference of two orthogonally polarized planes of laser radiation (red light) differing by a small frequency difference (supplied by the two frequency laser). More specifically, as the molecules align with the applied electrical field (in the POE chamber), the refractive index changes with molecular alignment, causing a phase difference in the transmitted radiation to be measured by the phase meter relative to a standard, sourced at the laser. The phase difference data obtained as a function of time (the period of field application) is digitized and stored on a computer for later retrieval and analysis. The exact instrumental requirements are as follows:

FIG. 18 is a schematic drawing of the instrumentation used. The laser 50 is dual frequency helium-neon (Optra Corp., Peabody, Mass.), and the emitted radiation is reflected off a mirror 52 to direct it through a miniature POE instrument 54 (identical to that exemplified in FIGS. 4 and 5 with the exception that this instrument measures 1 inch square). The radiation then passes through the POE chamber containing a transparent DNA- agarose gel insert as well as electrophoresis buffer (1/5×TBE) and finally, the transmitted radiation impinges on a detector 56 (silicon photodetector, PIN 3CD) connected to a UDT-201A amplifier (both from United Detector Technology, Hawthorne, Calif.). The signal from the detector amplifier (not shown in the schematic drawing) is fed to a phase meter 58 (Model 6000, Clarke-Hess Corp., NY, N.Y.) which determines the phase difference of the transmitted radiation with the reference signal sourced at the laser. The measured phase difference is digitized by a 12 bit analog to digital board (Lab Master, Scientific Solutions Corp., Solon, Ohio) installed in an IBM AT computer 60, and Unkel Scope software (Unkel Software, Inc., Cambridge, Mass.) is used for analog to digital board control and data analysis. The computer 60 also operates the pulse control through an Adtron DGS-16 (Adtron Corp., Gilbert, Ariz.) pulse synthesizer connected to relays powered by a Hewlett-Packard 6115A Precision Power Supply 62.

The miniature POE chamber and method was crucial to making possible the following experiment due to the ability of the bipolar isolated electrodes, as described herein, to allow back and forth motion of DNA particles, without any electrode induced field distortion in the POE chamber. The back and forth motion is not only a key feature of the POE method, but keeps the sample from moving out of the laser radiation. In other words, the POE chamber was able to deliver rapidly varying, homogeneous (uniform) fields.

Figure 19A:
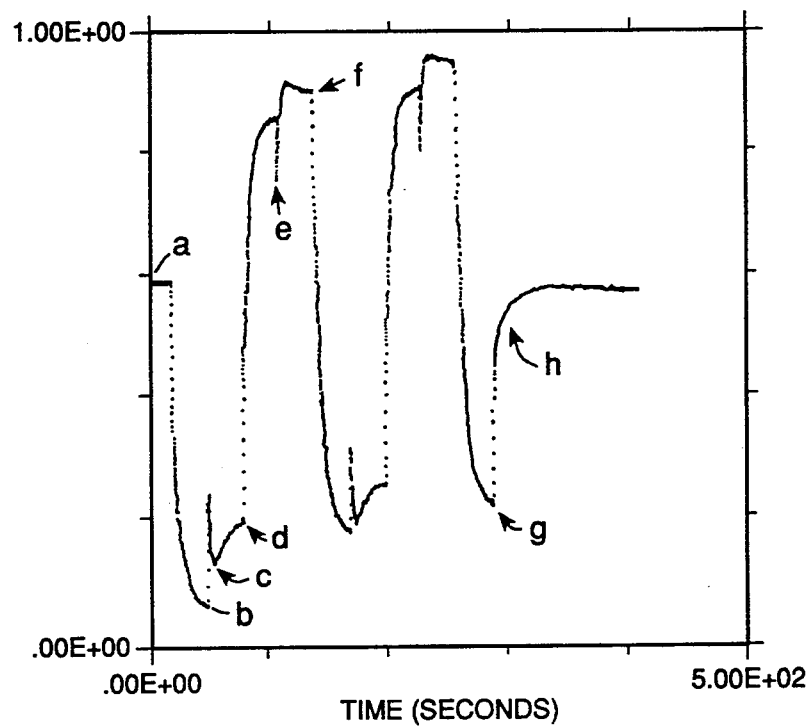
FIG. 19(a) shows the orientation of the lambda bacteriophage DNA molecules as produced by the pulsing routine of FIG. 19(b) (shaded boxes indicate field is on in given direction).
Figure 19B:
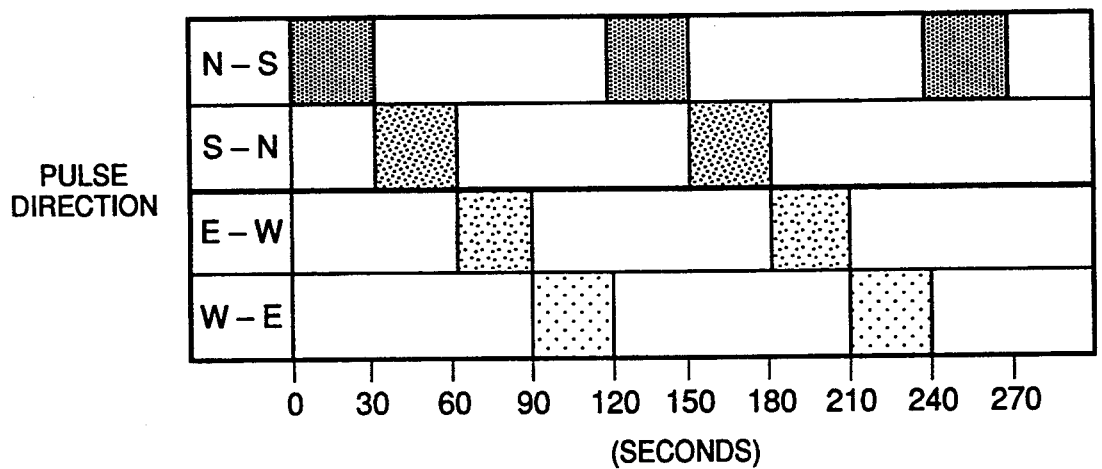
FIG. 19 shows the measurement of electrophoretically induced birefringence of concatenated lambda bacteriophage DNA molecules.

FIG. 19(a) shows the measurement (the vertical axis shows orientation, in arbitrary units, while the horizontal axis is time) of electrophoretically induced birefringence of lambda bacteriophage DNA molecules annealed in a small (80 microliter block of agarose) volume of agarose, using the instrumentation shown in FIG. 18 and the pulsing routine shown in FIG. 19(b). The annealing process produced concatamers (the DNA molecules stuck to each other through single stranded complementary strands at the ends) up to 2,000 kb in size as judged by POE analysis of ethidium stained gels. The gel block or insert contained 10 micrograms of DNA. The applied field strength was 25 volts/cm as measured by an external probe.

The data presented in FIG. 19(a) is analyzed as follows: (a) shows the baseline signal with no field applied, (b) indicates the orientation after a N-S pulse for 30 seconds (all pulses shown are 30 seconds long) and the start of S-N pulse terminates at (d), where an E-W pulse begins. At (e), the pulse is reversed to a W-E orientation and (f) shows the beginning of a N-S pulse. The pulsing continues as diagrammed in FIG. 19(b) until (g), when the field is shut off and the molecules relax as indicated by (h), to the initial baseline.

With the instrumentation shown in FIG. 18, it is possible to vary the effective field angle through the POE method and study its effect on molecular orientation. Thus, the POE method is applicable to electric field orientation studies using fluorescence and dichroic methods or the combination of both.

EXAMPLE 7

Separation of Large DNA Molecules Using the MPPE Method

*S. cerevisiae* samples were prepared as described in Example 1. Electrophoretic conditions were identical, with the exception that the step ratios used were equal to 1. The step time used was 3,3 seconds, with a switch time of 120 seconds, and the voltage ratio was 3:5 (75 volts N-S, 125 volts E-W-E). The running time was 48 hours.

Figure 20:
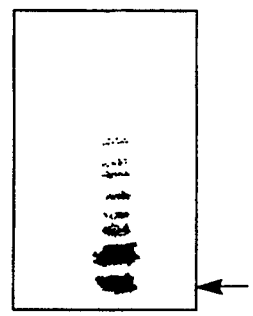
FIG. 20 illustrates Multiple Potential Pulsed Electrophoresis separation of S. cerevisiae chromosomal DNA molecules as described in Example 7. The figure shows the ethidium bromide stained gel containing S. cerevisiae with the arrow indicating the origin.

The results (see FIG. 20) show that the MPPE effect can modulate the electrophoretic velocity of large molecules, as well as size resolve them.

What is claimed as:

1. An apparatus for supporting a medium in which one or more samples of particles to be separated are placed for analytical electrophoresis comprising:
   a holder which fits neatly on a standard microscope stage;
   a slide which is placed into said holder and holds a medium in which one or more samples of particles to be separated are placed;
   a cover slip which encloses said slide;
   electrodes which make electrical contact between said slide and said cover slip; and
   an electrical connector placed on said holder which provides connection from said electrodes to bipolar diodes and means for varying electric fields from said electrodes.

2. An apparatus as in claim 1, in which one or more samples to be sized are placed for analytical electrophoresis.

* * * * *